United States Patent
Murdeshwar et al.

(10) Patent No.: US 11,717,656 B2
(45) Date of Patent: Aug. 8, 2023

(54) DELIVERY OF MIXED PHASE MEDIA FOR THE TREATMENT OF THE ANATOMY

(71) Applicant: GYRUS ACMI, INC., Southborough, MA (US)

(72) Inventors: Nikhil M. Murdeshwar, Maple Grove, MN (US); Thomas J. Holman, Princeton, MN (US)

(73) Assignee: Gyros ACMI Inc., Westborough, MA (US)

( * ) Notice: Subject to any disclaimer, the term of this patent is extended or adjusted under 35 U.S.C. 154(b) by 250 days.

(21) Appl. No.: 16/358,818

(22) Filed: Mar. 20, 2019

(65) Prior Publication Data

US 2020/0297983 A1  Sep. 24, 2020

(51) Int. Cl.
*A61M 31/00* (2006.01)
*A61B 18/02* (2006.01)
(Continued)

(52) U.S. Cl.
CPC ............ *A61M 31/00* (2013.01); *A61B 18/02* (2013.01); *A61M 13/003* (2013.01);
(Continued)

(58) Field of Classification Search
CPC .. A61M 2202/0275; A61M 2202/0283; A61M 2205/3368; A61M 2202/0007; A61M 11/02; A61M 2202/064; A61M 2205/05; A61M 2205/362; A61M 2202/03; A61M 2202/0225; A61M 2202/06; A61M 2210/14; A61M 2210/1433; A61M 2210/1475; A61M 2210/1425
See application file for complete search history.

(56) References Cited

U.S. PATENT DOCUMENTS 4,417,674 A * 11/1983 Giuffredi ............... B65D 83/48
222/402.18
4,617,064 A * 10/1986 Moore .................... B24C 1/003
134/11
(Continued)

FOREIGN PATENT DOCUMENTS

CN  111803203 A  10/2020
EP   1237610 A2   9/2002
(Continued)

OTHER PUBLICATIONS

CHANNEL Medsystems; 2.5 Minute Treatment; accessed on Nov. 3, 2018. http://www.channelmedsystems.com/cryothermic-ablation-procedure/.
(Continued)

*Primary Examiner* — Scott J Medway
(74) *Attorney, Agent, or Firm* — Schwegman Lundberg & Woessner, P.A.

(57) ABSTRACT

A medical device including an introducer; a first section configured to connect to a supply of therapeutic fluid; and a second section configured to connect to a supply of therapeutic elements. The therapeutic elements are drawn into the introducer by way of suction created by a flow of the therapeutic fluid through the introducer. The therapeutic elements are drawn into the introducer by way of suction created by a flow of the therapeutic fluid through the introducer.

19 Claims, 1 Drawing Sheet

(51) Int. Cl.
*A61M 13/00* (2006.01)
*A61B 18/00* (2006.01)

(52) U.S. Cl.
CPC ............. *A61B 2018/00559* (2013.01); *A61B 2018/0212* (2013.01); *A61M 2202/0225* (2013.01); *A61M 2202/0283* (2013.01); *A61M 2202/064* (2013.01); *A61M 2205/3653* (2013.01); *A61M 2206/10* (2013.01); *A61M 2210/1433* (2013.01)

(56) References Cited

U.S. PATENT DOCUMENTS

| | | | |
|---|---|---|---|
| 5,125,546 A * | 6/1992 | Dunne | B05B 7/0031 222/394 |
| 5,334,181 A * | 8/1994 | Rubinsky | A61B 18/02 606/26 |
| 5,460,628 A * | 10/1995 | Neuwirth | A61B 18/00 606/27 |
| 5,501,681 A | 3/1996 | Neuwirth et al. | |
| 5,910,104 A * | 6/1999 | Dobak, III | A61B 18/02 600/121 |
| 6,024,743 A | 2/2000 | Edwards | |
| 6,270,494 B1 * | 8/2001 | Kovalcheck | A61B 1/00142 600/121 |
| 6,306,119 B1 * | 10/2001 | Weber | A61M 37/00 604/290 |
| 6,368,074 B1 * | 4/2002 | Yamamoto | F04B 27/0895 417/269 |
| 6,398,775 B1 * | 6/2002 | Perkins | A61M 16/0459 604/102.03 |
| 6,517,533 B1 | 2/2003 | Swaminathan | |
| 7,625,368 B2 | 12/2009 | Schechter et al. | |
| 8,152,755 B1 * | 4/2012 | Wach | A61M 25/00 604/83 |
| 8,512,274 B2 | 8/2013 | Secovich et al. | |
| 9,392,935 B2 * | 7/2016 | Adams | A61B 17/42 |
| 9,974,592 B2 | 5/2018 | Baust et al. | |
| 2002/0010457 A1 | 1/2002 | Duchon et al. | |
| 2004/0092920 A1 | 5/2004 | Rozenshpeer | |
| 2005/0182397 A1 * | 8/2005 | Ryan | A61B 18/082 606/28 |
| 2005/0218007 A1 * | 10/2005 | Pekshev | A61M 15/02 205/615 |
| 2007/0088344 A1 | 4/2007 | Schechter | |
| 2007/0202106 A1 | 8/2007 | Palucka et al. | |
| 2008/0078382 A1 * | 4/2008 | LeMahieu | A61M 16/107 128/200.24 |
| 2008/0097468 A1 * | 4/2008 | Adams | A61B 17/12045 606/119 |
| 2009/0019886 A1 * | 1/2009 | Willen | F25J 1/0015 62/606 |
| 2009/0022805 A1 * | 1/2009 | Slager | A61P 43/00 424/486 |
| 2010/0043790 A1 * | 2/2010 | Tatarek | A61M 11/06 128/203.14 |
| 2010/0111854 A1 * | 5/2010 | Boyden | A61K 9/2866 424/1.49 |
| 2010/0121319 A1 * | 5/2010 | Chu | A61B 18/18 606/33 |
| 2010/0137857 A1 * | 6/2010 | Shroff | A61B 18/1815 606/33 |
| 2010/0239556 A1 * | 9/2010 | Rayner | A61K 35/33 424/94.4 |
| 2010/0323026 A1 * | 12/2010 | Sakai | A61P 9/10 424/501 |
| 2011/0178495 A1 * | 7/2011 | Ji | A61M 15/0016 606/213 |
| 2011/0251580 A1 * | 10/2011 | Greenhalgh | A61M 11/00 604/500 |
| 2012/0167878 A1 | 7/2012 | Belson et al. | |
| 2013/0178785 A1 * | 7/2013 | Papay | A61N 1/32 604/20 |
| 2014/0155745 A1 | 6/2014 | Duncan | |
| 2014/0200511 A1 * | 7/2014 | Boyden | A61K 9/1641 604/67 |
| 2015/0133779 A1 * | 5/2015 | Yurek | A61B 8/12 600/435 |
| 2016/0022345 A1 | 6/2016 | Baust et al. | |
| 2016/0220239 A1 * | 8/2016 | Keene | A61B 10/04 |
| 2017/0189627 A1 * | 7/2017 | Klever | A61M 19/00 |
| 2017/0265924 A1 | 9/2017 | Kochavi | |
| 2018/0028250 A1 * | 2/2018 | O'Connor | A61H 39/06 |
| 2018/0110554 A1 * | 4/2018 | Zarins | A61B 18/1482 |
| 2018/0125561 A1 | 5/2018 | Burnett et al. | |
| 2018/0133446 A1 * | 5/2018 | Shikhman | A61M 25/10 |
| 2018/0236214 A1 | 8/2018 | Levy et al. | |
| 2018/0360424 A1 | 12/2018 | Yurek et al. | |
| 2019/0070397 A1 | 3/2019 | Levy et al. | |
| 2019/0307948 A1 * | 10/2019 | Levy | A61M 25/0068 |
| 2019/0321570 A1 * | 10/2019 | Rubin | A61M 11/041 |
| 2020/0146739 A1 * | 5/2020 | Klever | A61M 11/02 |
| 2020/0261707 A1 * | 8/2020 | Shikhman | A61B 18/06 |

FOREIGN PATENT DOCUMENTS

| | | | |
|---|---|---|---|
| EP | 2753273 A1 | 7/2014 | |
| EP | 3146925 A1 | 3/2017 | |
| WO | WO-02055139 A1 | 7/2002 | |

OTHER PUBLICATIONS

"Chinese Application Serial No. 202010200444.5, Notification to Make Rectification mailed May 6, 2020", w/o English Translation, 1 pg.
"Chinese Application Serial No. 202010200444.5, Notification to Make Rectification mailed Jul. 27, 2020", w/o English Translation, 1 pg.
"Chinese Application Serial No. 202010200444.5, Response filed Jun. 23, 2020 to Notification to Make Rectification mailed May 6, 2020", w/o English Claims, 5 pgs.
"Chinese Application Serial No. 202010200444.5, Response filed Aug. 20, 2020 to Notification to Make Rectification mailed Jul. 27, 2020", w/o English Claims, 3 pgs.
"European Application Serial No. 20164296.4, Extended European Search Report dated Oct. 2, 2020", 13 pgs.
"European Application Serial No. 20164296.4, Partial Supplementary European Search Report dated Jul. 24, 2020", 11 pgs.
"European Application Serial No. 20164296.4, Response filed May 3, 2021 to Extended European Search Report dated Oct. 2, 2020", 10 pgs.

* cited by examiner

DELIVERY OF MIXED PHASE MEDIA FOR THE TREATMENT OF THE ANATOMY

FIELD

These teachings relate to a medical device and method for treating the anatomy.

BACKGROUND

Menorrhagia is a medical condition that includes abnormally heavy and prolonged menstrual bleeding and pain. For decades, hormone pills and/or hysterectomy were used to treat menorrhagia.

Recently, medical devices have been introduced to treat menorrhagia by way of endometrium ablation, where the endometrium is exposed to various treatment modalities such as RF energy, thermal energy, microwave energy, and/or steam. Some example medical devices are disclosed in US2018/0125561 and US20170265924, which are incorporated by reference herein for all purposes.

It may be desirable to have a medical device and/or method that is configured to improve treatment time of the anatomy. For example, it may be desirable to have a medical device and/or method that is configured to prolong endometrium ablation beyond treatment time after completion of a medical procedure and/or after the medical device has been removed from the anatomy.

SUMMARY

These teachings provide a medical device. The medical device is configured to improve treatment time of the anatomy. The medical device and/or method according to these teachings is configured to prolong ablation beyond treatment time after completion of a medical procedure and/or after the medical device has been removed from the anatomy.

These teachings provide a medical device including an introducer; a first section; and a second section. The first section is configured to connect to a supply of therapeutic fluid. The second section is configured to connect to a supply of therapeutic elements. The therapeutic elements are drawn into the introducer by way of a venturi effect or suction created by a flow of the therapeutic fluid through the introducer.

These teachings provide a medical device that includes an introducer; a supply of therapeutic fluid configured to pass through the introducer; and a supply of therapeutic elements configured to pass through the introducer. The therapeutic elements are drawn into the introducer by way of suction.

These teachings provide a medical device that includes an introducer comprising a narrowed section; a first section configured to connect to a supply of therapeutic fluid, the therapeutic fluid is configured to flow through the introducer and the narrowed section; and a second section configured to connect to a supply of therapeutic elements. The therapeutic elements are drawn into the introducer by way of a venturi effect or suction created by the flow of the therapeutic fluid through the narrowed section.

These teachings provide a method that includes: inserting the introducer of the medical device according to the teachings herein into the anatomy; configuring the therapeutic fluid to flow through the introducer; and after the configuring step, the method includes a step of configuring the therapeutic elements to be drawn into the introducer by way of the venturi effect or suction; and supplying a mixture of the therapeutic elements and the therapeutic fluid into the anatomy.

DETAILED DESCRIPTION

Figure 1:
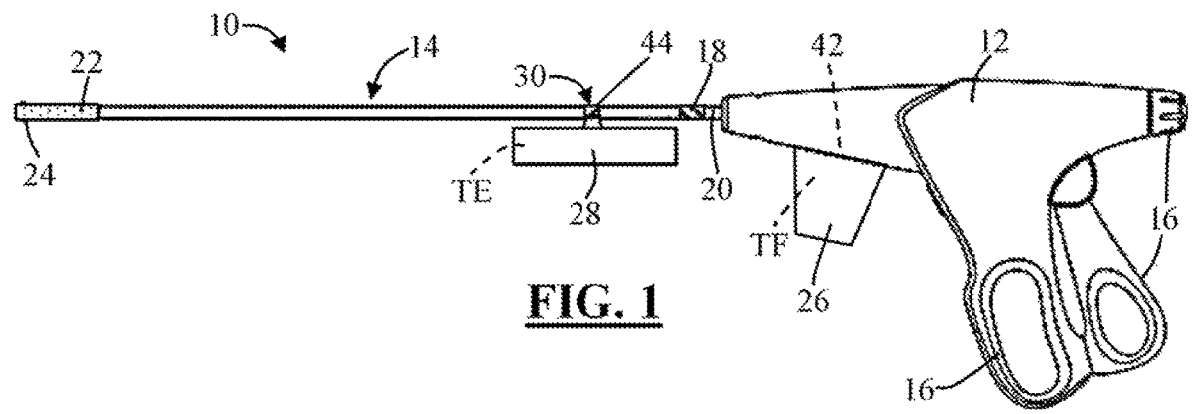
FIG. 1 is a side view of a medical device.

These teachings relate to a medical device. The medical device may be used to treat or effect an anatomical feature. The anatomical feature may be any anatomical feature, such as a body cavity or a body lumen. The body cavity may be a uterus. The medical device may be configured to treat menorrhagia. The medical device may be configured to effect or destroy the endometrium by way of cryogenics.

While the medical device disclosed herein may be used to treat menorrhagia, it is understood that the medical device can be used in other applications as well. For example, the device and system can be used to treat tissue in the bladder, vagina, esophagus, trachea, urethra, ureter, prostate gland, kidney, intestinal growths or abnormal tissues of the intestine, cancerous tissue, etc.

The medical device may be configured to supply or deliver a therapeutic fluid into the anatomy. The medical device may be configured to supply or deliver therapeutic elements into the anatomy. The medical device may be configured to supply or deliver both therapeutic fluid and therapeutic elements into the anatomy. Stated another way, the medical device may be configured to supply or deliver a mixed phase medical into the anatomy to treat the anatomy.

The medical device according to these teachings is configured to provide global treatment of a body cavity like the uterus. That is, by supplying a flow of the therapeutic fluid and therapeutic elements into the anatomy, a global or full surface of the tissue of the body cavity can be treated at substantially the same time, as opposed to locally or discretely treating the tissue as may be the case with other medical devices that utilize forceps or a wire electrode, for example.

The medical device comprises a hand piece. The hand piece may function to be held by a user or robot and/or support or contain one or more components of the medical device. For example, the hand piece may support or contain one or more elements or devices for treating the anatomy and/or for operating the medical device.

The medical device and/or the hand piece may comprise one or more user controls. Movement or manipulation of the one or more user controls may function to move or actuate the introducer, activate or de-activate one or more modalities for treating the anatomy. Movement or manipulation of the one or more user controls may function to start, stop, slow, or speed up a flow of therapeutic fluid in fluid communication in the medical device. Movement or manipulation of the one or more user controls may function to increase or decrease a temperature of the therapeutic fluid.

Movement or manipulation of the one or more user controls may function to supply or cease suppling or increase or decrease a supply of the one or more of the therapeutic elements into the flow of therapeutic fluid. For example, movement or manipulation of the one or more user controls may function to open or close an opening, port or door located between the introduction port and the contrasted section thus allowing or preventing the therapeutic elements to be or from being suctioned into the flow of the therapeutic fluid. Movement or manipulation of the one or more user controls may function to increase or decrease the amount or number of therapeutic elements released into the flow of the therapeutic fluid by increasing or decreasing a size of an opening of the introduction port or tube between the supply of therapeutic elements and the constricted section.

The one or more user controls may be one or more switches, levers, buttons, triggers, knobs, rotation wheels, or a combination thereof. The one or more user controls may also be a foot pedal in communication with the medical device.

The medical device comprises an introducer. The introducer may function to permit a portion of the medical device to be inserted into a patient or the anatomy, while a portion of the device remains outside of the patient or anatomy.

The introducer may be a tubular member. The introducer may be a braided or coiled tube. The introducer may be a tube that is generally smooth on the inside and outside surfaces. The introducer may be an elongated member that extends along a longitudinal axis. The proximal end or proximal portion of the introducer may be connected to the hand piece. The introducer may have a relatively small diameter, on the order of about 10 mm or less, 9 mm or less, 8 mm or less, 7 mm or less, or even 6 mm or less. Preferably, the diameter of the introducer may be less than 5 mm. Such relatively small sized introducer may be advantageous in minimizing patient trauma during insertion and/or removal of the introducer into and from a body lumen and/or body cavity.

The introducer may be substantially straight and/or may include sections that are substantially straight; may include one or more angles, bends or arcs and/or may include sections that have one or more angles, bends or arcs; or a combination thereof. The introducer may be substantially rigid, substantially flexible, substantially resilient, substantially kink-resistant, or a combination thereof. The introducer may be configured in such a way to allow angular movements and/or can be advanced along a tortuous path within a body lumen and/or body cavity.

The introducer may comprise an internal channel or lumen. The channel or lumen may be configured to direct, deliver, or transport the therapeutic fluid, the therapeutic elements, or a mixture of both of the therapeutic fluid and therapeutic elements into the anatomy.

The introducer may have a plurality of channels or lumen. Each channel or lumen may be configured to direct, deliver, or transport the same therapeutic fluid, the same therapeutic elements, or a mixture of both of the therapeutic fluid and therapeutic elements into the anatomy, or each channel or lumen may be configured to direct, deliver, or transport different therapeutic fluid, different therapeutic elements, or a different mixture of the therapeutic fluid and therapeutic elements into the anatomy. This means that during a medical procedure, various therapeutic fluid, elements, and mixtures thereof can be delivered into the anatomy at the same time or at different times during the procedure.

The medical device comprises one or more expanders. The expander may function to reduce a temperature of the therapeutic fluid. The expander may function to reduce a temperature of the therapeutic fluid to a cryogenic temperature. The expander may be an expansion valve. The cryogenic temperature of the therapeutic fluid may be at or below approximately −180° C. The cryogenic temperature may be in a range of approximately −150° C. (−238° F.) to absolute zero (−273° C. or −460° F.). A temperature of the therapeutic fluid may be on the order of about 0 degrees Celsius or less, −10 degrees Celsius or less, −20 degrees, −85 degrees Celsius or less, −90 Celsius or less, etc.

The expander may be located downstream or distal of the first section or the supply of the therapeutic fluid. The expander may be located in between the first section and the second section. The expander may be located downstream or distal of the second section and also downstream or distal of the first section.

The medical device comprises a constricted section. The constricted section may function to increase a velocity of the flow of therapeutic fluid, decrease a pressure of the therapeutic fluid, or both. The constricted section may function to create a vacuum or a localized vacuum as a result of a flow of the therapeutic fluid through the constricted section.

The constricted section may function to create and/or apply a venturi effect to the therapeutic fluid passing or flowing through the constricted section, which causes the therapeutic elements to be drawn into, or suctioned into, the flow of the therapeutic fluid to create a mixture of the therapeutic fluid and therapeutic elements.

The constricted section may be a narrowed, tapered, or reduced cross section of the introducer or tube or passageway defined between the supply of therapeutic fluid and a distal end of the medical device. The constricted section may be hourglass shaped, such that it is relatively wide at a proximal end portion, tapers radially inwardly to a constricted portion, and then tapers radially outward form the constricted portion to a distal end portion.

The constricted section may be a coke of a pipe. The constricted section may be created by inserting a member inside of the introducer to reduce the inner diameter thereof while the outer diameter at the constricted section remains generally the same as the rest of the introducer. The constricted section may be created by locally narrowing the outer and inner diameter of the introducer.

The medical device may comprise one or more introduction ports at each constricted section. Advantageously, this means that more than one type of therapeutic element may be mixed with the therapeutic fluid(s) at the constricted section for delivery into the anatomy. The introduction of the therapeutic elements (i.e., the location of the introduction) may be at the constricted section or at a location distal of the constricted section where a venturi effect can still be applied to draw or suction the therapeutic elements into the flow of the therapeutic fluid.

The medical device may comprise more than one constricted section. This may be desirable to add different therapeutic elements into the flow of the therapeutic fluid at various locations before being deposited into the anatomy. This may also be desirable to adjust a flow or pressure of the therapeutic fluid before entry into the anatomy.

The medical device comprises one or more effectors. The effector is configured to deliver the therapeutic fluid, the therapeutic elements, or a mixture of both of the therapeutic fluid and therapeutic elements into the anatomy. The effector may be located at a distal-most end of the introducer, at a distal end of the introducer, or anywhere along a length of the introducer, or a combination thereof.

The effector may comprise one or more: nozzles, valves, expanders, orifices, holes, fissures, slots, or other openings so that the therapeutic fluid, the therapeutic elements, or a mixture of both can be released from within the introducer to a site of interest.

The therapeutic fluid may function to effect the anatomy, tissue or features defining the anatomy, a body cavity, a body lumen, or a combination thereof. For example, the therapeutic fluid may function to heat or cool tissue inside of a body cavity and/or therapeutic elements. The therapeutic fluid may function to treat or destroy the endometrium inside of the uterus. The therapeutic fluid may function to freeze the endometrium inside of the uterus.

The therapeutic fluid may be any fluid, such as a liquid, gas, or both. The therapeutic fluid may be nitrous oxide, liquid nitrogen, carbon dioxide, argon, nitrogen, krypton, the like, or a combination thereof. The therapeutic fluid may be a cryogenic fluid. The therapeutic fluid may be air.

A temperature of the therapeutic fluid may be cooled or chilled to a cryogenic temperature, which may be at or below approximately −180° C. The cryogenic temperature may be in a range of approximately −150° C. (−238° F.) to absolute zero (−273° C. or −460° F.). A temperature of the therapeutic fluid may be on the order of about 0 degrees Celsius or less, −10 degrees Celsius or less, −20 degrees, −85 degrees Celsius or less, −90 Celsius or less, etc. The therapeutic fluid may be cooled or chilled with an expander.

Alternatively, the therapeutic fluid may be not cooled; instead, the therapeutic fluid may be heated, or at room temperature, or heated to a temperature above room temperature. Room temperature may be about 70° F. Room temperature may be less than 70° F. Room temperature may be greater than 70° F.

The therapeutic fluid may be supplied to the medical device from a supply of a therapeutic fluid. The supply of the therapeutic fluid may be a canister, cartridge, pouch, bag, drum, or other container that is directly connected to the medical device, the hand piece, and/or the introducer.

The supply of the therapeutic fluid may be received into or connected to a port, housing, channel or guide defined in or on the medical device, the hand piece, and/or the introducer. Additionally, or alternatively, the supply of the therapeutic fluid may be located at a remote location from the medical device, the hand piece, and/or the introducer and connected thereto via one or more tubes or hoses. Preferably, the supply of the therapeutic fluid is supplied or provided into the medical device, the hand piece, and/or the introducer at a location that is proximal to the supply of the therapeutic elements.

The medical device may comprise one supply of the therapeutic fluid. The device may comprise multiple supplies of therapeutic fluid, each of which may comprise the same or different therapeutic fluid. For example, the medical device may comprise a plurality of supplies of the therapeutic fluid that can be delivered individually or as a mixture through the introducer and into the anatomy. Each of the different therapeutic fluids may be provided into a common lumen in the introducer, or into individual lumen in the introducer. Each of the different therapeutic fluids may be provided into a common constricted section, or into individual constricted sections that are sized to accommodate a particular type of fluid and element.

The therapeutic elements may function to effect the anatomy, tissue or features defining the anatomy, a body cavity, a body lumen, or a combination thereof. For example, the therapeutic elements may function to heat or cool tissue inside of a body cavity. The therapeutic elements may function to treat or destroy the endometrium inside of the uterus. The therapeutic fluid may function to freeze or destroy the endometrium inside of the uterus.

The therapeutic elements may be provided into a flow or stream of the therapeutic fluid flowing through the medical device and/or effector, and then may be carried in the flow or stream of the therapeutic fluid into the anatomy or body cavity. The therapeutic elements may be aimed or directed at or towards an anatomical feature and configured to be embedded and/or impact into the anatomical feature at a high velocity of the therapeutic fluid. By impacting the anatomy or the tissue of the body cavity, the therapeutic elements may function to soften, treat, or destroy the tissue.

The therapeutic elements may be configured to absorb, hold, and/or transfer thermal energy from the therapeutic fluid or other temperature source after the therapeutic elements are mixed with the therapeutic fluid. For example, if the therapeutic fluid or temperature source is a cryo-energy, then the therapeutic fluid is configured to absorb, hold, and/or transfer the cryogenic energy from the therapeutic fluid to the anatomical feature. For example, if the therapeutic fluid is a heated fluid such as saline or heater such as a resistive heater, then the therapeutic elements may be configured to absorb, hold, and/or transfer the heated energy from the therapeutic fluid to the anatomical feature.

The therapeutic elements may be configured to hold thermal energy from the therapeutic fluid, and then after being embedded in the tissue or anatomy, the therapeutic elements are configured to transfer or dissipate the thermal energy into the anatomy or tissue in the body cavity even after the medical device or introducer is removed from the anatomy. Stated another way, ablation or treatment time of the anatomy can continue even after the medical procedure has been completed and/or the device has been removed from within the anatomy. Advantageously, this means that medical procedure times can be shortened while increasing treatment times.

The therapeutic elements may be or comprise one or more of the following: biodegradable elements, metal elements, balls, powder, solid particles, pellets, a biodegradable polymer matrix, a non-swellable polymer (e.g., PLGA or poly (ortho ester), a swellable polymer such as, with hydrogels, or a combination thereof. The therapeutic elements may comprise high specific heat (thermal mass). For example, the therapeutic elements may have a high specific heat or thermal mass that is greater than a specific heat of the tissue or the anatomy or therapeutic fluid. The therapeutic elements comprise a material having a specific heat that is greater than a specific heat of the therapeutic fluid. The therapeutic elements may be made from magnesium, iron. The therapeutic elements may be implanted within a biodegradable polymer matrix, and formulated for sustained release of a therapeutic agent. This means that the therapeutic agent may be released from the therapeutic elements for an extended period of time, even after the medical device has been removed from within the anatomy. Advantageously, this means that treatment time of the anatomy may continue even after the medical device has been removed from within the anatomy. The therapeutic elements may comprise, or the therapeutic agent released by the therapeutic elements may be, a pain killer, an antibiotic, a steroidal anti-inflammatory agent, or a combination thereof. The therapeutic elements may be configured to release a therapeutic agent after being implanted in the anatomical feature or anatomy. The therapeutic elements may be contained or mixed with a carrier fluid, so that when the therapeutic elements are drawn or suctioned up into the flow of the therapeutic fluid, the carrier fluid is also drawn or suctioned into the flow of the therapeutic fluid. Mixing the therapeutic elements with the carrier fluid may assist with drawing or suctioning up the therapeutic elements into the flow of the therapeutic fluid. The carrier fluid may be the same as the therapeutic fluid. The carrier fluid may be water or saline or a gas.

A temperature of the therapeutic elements may be cooled or chilled to a cryogenic temperature, which may be at or below approximately −180° C. The cryogenic temperature may be in a range of approximately −150° C. (−238° F.) to absolute zero (−273° C. or −460° F.). A temperature of the therapeutic fluid may be on the order of about 0 degrees Celsius or less, −10 degrees Celsius or less, −20 degrees Celsius or less, −40 degrees Celsius or less, −60 degrees Celsius or less, −80 degrees Celsius or less, −85 degrees Celsius or less, −90 Celsius or less, etc. The therapeutic elements may be cooled or chilled by way of thermal transfer from a temperature of the therapeutic fluid that is configured to move or pass the therapeutic fluid through the medical device and introducer into the anatomy. In other words, the therapeutic fluid may be cooled or cold, and the temperature of the therapeutic fluid may be transferred to the therapeutic elements to cool or lower a temperature of the therapeutic elements.

The therapeutic elements may be contained or stored in a supply or source of the therapeutic elements. The supply or source of the therapeutic elements may be a canister, cartridge, pouch, bag, drum, or other container that is directly connected to the medical device, the hand piece, and/or the introducer or connected thereto via a hose or tube.

FIG. 1 illustrates a medical device 10. The medical device 10 comprises a hand piece 12 and an introducer 14. The hand piece 12 is configured to be gripped or held by a user. The hand piece 12 comprises one or more user controls 16 for operating, manipulating, and/or using the medical device 10. The introducer 14 extends along a longitudinal axis and has a proximal end 20 connected to the hand piece 12. The introducer 14 comprises an effector 22 at its distal end 24.

The medical device 10 comprises a first section 42 that is configured to connect to a supply or source of therapeutic fluid 26 comprising therapeutic fluid TF. The therapeutic fluid TF may be nitrous oxide.

The medical device 10 comprises a second section 44 configured to connect to a supply or source of therapeutic elements 28 comprising therapeutic elements TE. The therapeutic elements TE may be biodegradable elements, metal balls, a powder, or a combination thereof.

The second section 44, or the supply or source of the therapeutic elements 28 is connected to the medical device 10 at a constricted section 30. Preferably, the first section 42 where the supply or source of the therapeutic fluid 26 is connected to the medical device 10 is located proximal or upstream relative to the constricted section 30 and the second location 44 of the medical device 10 where the supply or source of the therapeutic elements 28 is connected.

The medical device 10 comprises an expander 18. The expander 18 is configured to expand therapeutic fluid TF so that a temperature of the therapeutic fluid TF is lowered or reduced. The temperature of the therapeutic fluid TF may be lowered to a cryogenic temperature. The expander 18 may be an expansion valve. The expander 18 is located downstream or distal of the first section 42 or the supply 26 of the therapeutic fluid TF. The expander 18 is located between the first section 26 and the second section 28. In some configurations, the expander 18 may be located downstream or distal of the second section 28.

Figure 2:
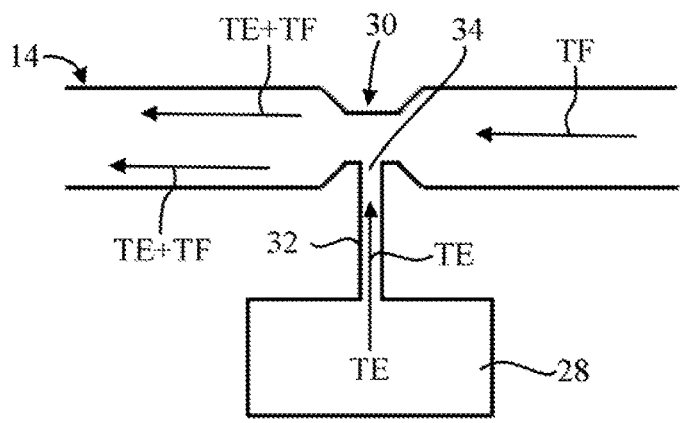
FIG. 2 is a cross-sectional view of a portion of the medical device of FIG. 1.

Referring to FIG. 2, the constricted section 30 of the medical device 10 (FIG. 1) is a narrowed, tapered, or reduced cross section of the introducer 14. The constricted section 30 is configured to increase a fluid velocity of the therapeutic fluid TF passing through the introducer 14, while decreasing a fluid pressure of the therapeutic fluid TF passing through the introducer 14 and/or the constricted section 30 as the therapeutic fluid TF flows towards the effector 22 (FIG. 1).

The medical device 10 comprises an introduction port 32. The introduction port 32 is an opening, passageway, port, or tube through which therapeutic elements TE from the supply or source of the therapeutic elements 28 are configured to be introduced into the constricted section 30 and/or into the introducer 14 and/or into the flow of the therapeutic fluid TF passing through the medical device 10 and/or introducer 14.

As will be discussed below, during use, the therapeutic fluid TF is configured to flow through the introducer 14 towards the effector 22 and/or the distal end 24 of the introducer 14 (i.e., in the left direction in FIGS. 1-3). As the therapeutic fluid TF flows through the constricted section 30, a fluid velocity of the therapeutic fluid TF increases while a fluid pressure of the therapeutic fluid TF decreases, which creates a localized vacuum in the constricted section 30 or generally in the location of the introduction port 32 relative to the supply 28 of the therapeutic elements TE. The localized vacuum or venturi effect created by the flow of the therapeutic fluid FT through the constricted section 30 causes the therapeutic elements TE to be drawn up, or brought up, or suctioned into the introducer 14 and/or into the flow of the therapeutic fluid TF flowing or passing through the introducer 14. The therapeutic elements TE are then mixed with the therapeutic fluid TF inside of the introducer 14 as the therapeutic fluid TF continues to flow towards the effector 22 or distal end 24 of the introducer 14.

Figure 3:
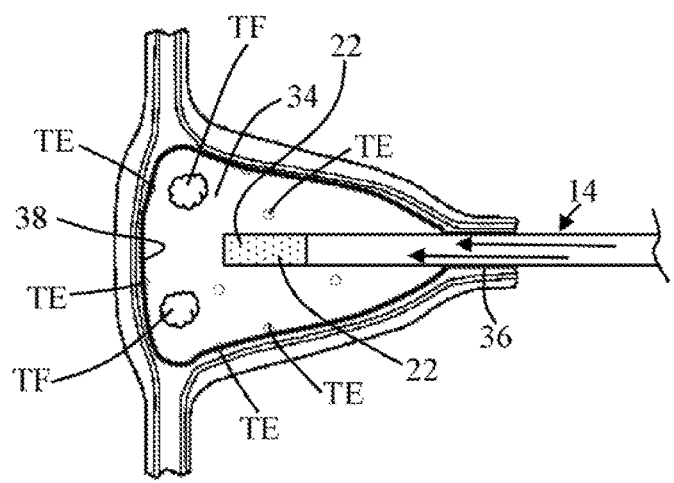
FIG. 3 is a cross-sectional view of a portion of the medical device of FIG. 1 located inside of a body cavity.

Referring now to FIG. 3, the introducer 14 is illustrated inside of the anatomy. More specifically, the introducer 14 has been inserted into a body cavity 34, which may be a uterus, through a body lumen 36, which may be the internal os.

Referring to FIGS. 1-3, the medical device 10 can be used in a medical procedure. It is understood that the order of the method steps described herein can change or be rearranged. For example, one or more steps can be repeated, omitted, or combined with other steps. One or more of the method steps described herein can be separated into one or more sub-steps, and one or more of those sub-steps can be repeated, omitted, or combined with other steps or sub-steps.

Before, during or after insertion or placement or implantation of the effector 22 or distal end 24 of the introducer 14 into the anatomy, one or more of the user controls 16 may be manipulated so that the medical device 10 delivers or supplies the therapeutic fluid TF from the supply or source of the therapeutic fluid 26 (FIG. 1), through the introducer 14, and into the anatomy through the effector 22. The flow of the therapeutic fluid TF may be directed to contact with the uterus or the interior uterine surface or wall. The flow of the therapeutic fluid TF may be directed into direct contact with the uterus or the interior uterine surface or wall. The therapeutic fluid TF may function to effect tissue in the anatomy, such as the endometrium in the uterus.

The therapeutic fluid TF may pass through the expander 18, which may function to reduce or cool a temperature of the therapeutic fluid TF. The therapeutic fluid TF may be cooled to a cryogenic temperature.

As the therapeutic fluid TF flows or passes through the constricted section 30, a fluid velocity of the therapeutic fluid TF increases, while a fluid pressure of the therapeutic fluid TF decreases, which is configured to draw or suction or introduce the therapeutic elements TE from the source 28 into the flow of the therapeutic fluid TF to create a mixture thereof. The therapeutic elements TE may be introduced into the flow of the therapeutic fluid TF by way of a venturi effect. A temperature of the therapeutic elements TE may be reduced, even reduced to a cryogenic temperature by being mixed with the cooled or cryogenic temperature of the therapeutic fluid TF which was cooled after the therapeutic fluid TF passed through the expander 18. The mixture of the therapeutic fluid TF and the therapeutic elements TE is then configured to be expelled into the anatomy via the effector 22. The therapeutic elements TE are configured to be discharged through the effector 22 and directed at the anatomy, tissue, walls, or anatomical features defining the body cavity 34. The body cavity 34 may be a uterus. The therapeutic elements TE are configured to contact and/or impact the body cavity 34 and/or at least partially embed into the body cavity 34 or tissue, wall, or anatomical feature defining the body cavity 34. The therapeutic elements TE may be configured to transfer temperature (heat or cold) from the therapeutic fluid TF into the anatomy to medically effect the anatomy or tissue defining the body cavity 34. Stated another way, if the therapeutic fluid TF is cooled through the expander 18, then the therapeutic elements TE may also be cooled by way of thermal transfer from the therapeutic fluid TF to the therapeutic elements TE, which may then be transferred to the anatomy or tissue defining the body cavity 34 after the therapeutic elements TE contact or are embedded in the anatomy.

The therapeutic elements TE may be configured to hold or maintain thermal energy from the therapeutic fluid TF, and then after being embedded in the tissue or the body cavity 34, the therapeutic elements TE may be configured to continue to transfer or dissipate the thermal energy into the body cavity 34 or anatomy defining the cavity 34 even after the medical device 10 or introducer 14 has been removed from the body cavity 34. Stated another way, ablation or treatment time of the body cavity 34 can continue even after the medical procedure has been completed and/or after the device 10 has been removed from within the body cavity 34. Moreover, because the therapeutic elements TE have a specific heat, the therapeutic elements TE may be configured to continue to transfer or dissipate the thermal energy into the body cavity 34 even after the therapeutic TF has warmed up inside of the body cavity 34 and is no longer at the cryogenic temperature Advantageously, this means that the time required for the actual medical procedure can be shortened while the treatment time increases.

Before, during, or after the medical procedure, the supply or source of the therapeutic elements 28 can be controlled (via the one or more user controls 16, for example) so that only the therapeutic fluid TF is supplied into the anatomy, or the amount of the therapeutic elements 28 supplied into the anatomy can be increased or decreased by manipulating the amount and speed of the flow of the therapeutic fluid TF.

The medical device 10 may include multiple supplies or sources of therapeutic fluid 26 and/or multiple supplies or sources of the therapeutic elements 28. The supply of the various therapeutic fluids TF and therapeutic elements TE can be located anywhere on the medical device 10 and/or introducer 14.

The supply of various therapeutic fluids TF and therapeutic elements TE can be controlled or fine-tuned, depending on the medical procedure. For example, a first therapeutic fluid may be supplied into the anatomy with first therapeutic elements followed by a second therapeutic fluid and/or second therapeutic elements. For example, a first therapeutic fluid may be supplied into the anatomy with first therapeutic elements in combination with a second therapeutic fluid and/or second therapeutic elements. The various therapeutic fluids and/or therapeutic elements may flow or may be mixed in a common introducer 14 and/or constricted section 30. The various therapeutic fluids and/or therapeutic elements may flow in separate and discrete lumen defined in the introducer 14 and/or separate or discrete constricted sections 30 in the medical device 10.

In another configuration of the medical device 10 and/or the method of using the medical device 10, the medical device 10 may be free of an expander 18, or the flow of the therapeutic fluid TF may bypass the expander 18, so that the therapeutic fluid is not cooled or reduced to a cryogenic temperature. The flow of the therapeutic fluid TF can pass through one or more constricted sections 30 so that therapeutic elements TE are drawn into or suctioned into or provided into the flow of the therapeutic fluid TF. The mixture of the therapeutic fluid TF and the therapeutic elements TE can then be delivered directly into the body cavity or uterus and directed at the walls or tissue defining the uterus.

In another configuration of the medical device 10 and/or the method of using the medical device 10, the therapeutic fluid TF may pass through the expander 18, which may function to reduce or cool a temperature of the therapeutic fluid TF to a cryogenic temperature, for example. The flow of the therapeutic fluid TF can then be delivered directly into the body cavity or uterus and directed at the walls or tissue defining the uterus. That is, the medical device 10 may be free of a constricted section 30, or the constricted section 30 may be bypassed so that therapeutic elements TE are not drawn into or suctioned into or provided into the flow of the therapeutic fluid TF and only the therapeutic fluid TF is delivered directly into the body cavity or uterus and directed at the walls or tissue defining the uterus.

A method comprising reducing a temperature of a therapeutic fluid to a cryogenic temperature; and directing a flow of the therapeutic fluid into a uterus. The method comprises introducing therapeutic elements into the flow of the therapeutic fluid. The therapeutic elements are introduced into the flow of the therapeutic fluid by way of a venturi effect.

A method comprising reducing a temperature of particles to a cryogenic temperature; and directing a flow of the particles into a uterus. The method comprises reducing a temperature of a therapeutic fluid to a cryogenic temperature. The method comprises introducing the particles into a flow of the therapeutic fluid by way of suction.

LISTING OF REFERENCE NUMERALS 10 medical device
12 hand piece
14 introducer
16 user controls
18 expander
20 proximal end
22 effector
24 distal end
26 source of therapeutic fluid
28 source of therapeutic elements
30 constricted section
32 introduction port
34 body cavity
36 body lumen
38 anatomical feature
42 first section
44 second section
TE therapeutic element
TF therapeutic fluid The explanations and illustrations presented herein are intended to acquaint others skilled in the art with the invention, its principles, and its practical application. The above description is intended to be illustrative and not restrictive. Those skilled in the art may adapt and apply the invention in its numerous forms, as may be best suited to the requirements of a particular use.

Accordingly, the specific embodiments of the present invention as set forth are not intended as being exhaustive or limiting of the teachings. The scope of the teachings should, therefore, be determined not with reference to this description, but should instead be determined with reference to the appended claims, along with the full scope of equivalents to which such claims are entitled. The omission in the following claims of any aspect of subject matter that is disclosed herein is not a disclaimer of such subject matter, nor should it be regarded that the inventors did not consider such subject matter to be part of the disclosed inventive subject matter.

Plural elements or steps can be provided by a single integrated element or step. Alternatively, a single element or step might be divided into separate plural elements or steps.

The disclosure of "a" or "one" to describe an element or step is not intended to foreclose additional elements or steps.

While the terms first, second, third, etc., may be used herein to describe various elements, components, regions, layers and/or sections, these elements, components, regions, layers and/or sections should not be limited by these terms. These terms may be used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

The disclosures of all articles and references, including patent applications and publications, are incorporated by reference for all purposes. Other combinations are also possible as will be gleaned from the following claims, which are also hereby incorporated by reference into this written description.

The invention claimed is:

1. A medical device comprising:
    an introducer extending along a longitudinal axis and having a proximal end, a distal end, an internal lumen extending from the proximal end to the distal end and defining a first cross-sectional diameter in a plane substantially perpendicular to the longitudinal axis, and a constricted section within the internal lumen defining a second cross-sectional diameter in a plane substantially perpendicular to the longitudinal axis that is less than the first cross-sectional diameter;
    a first section configured to connect to a supply of therapeutic fluid, the first section disposed adjacent to the proximal end of the introducer;
    a second section configured to connect to a supply of therapeutic elements, the second section connected to the introducer at the constricted section, the therapeutic elements comprising solid particles that are implantable within human body tissue; and
    an expander located between the first section and the constricted section that is configured to reduce a temperature of the therapeutic fluid to a cryogenic temperature lower than a temperature of the therapeutic elements;
    wherein the therapeutic elements are drawn into the introducer at the constricted section by way of suction created by a flow of the therapeutic fluid through the introducer.

2. The medical device according to claim 1, further comprising a supply of therapeutic fluid, wherein the therapeutic fluid is carbon dioxide.

3. The medical device according to claim 1, further comprising a supply of therapeutic elements, wherein the therapeutic elements comprise powder.

4. The medical device according to claim 1, further comprising a supply of therapeutic elements, wherein the therapeutic elements comprise metal balls.

5. The medical device according to claim 1, further comprising a supply of therapeutic elements, wherein the therapeutic elements are implanted within a biodegradable polymer matrix, and configured for sustained release of a therapeutic agent.

6. The medical device according to claim 1, further comprising a supply of therapeutic elements, wherein the therapeutic elements are configured to be implanted in an anatomical feature.

7. The medical device according to claim 6, wherein the therapeutic elements are configured to release a therapeutic agent after being implanted in the anatomical feature.

8. The medical device according to claim 1, further comprising an effector located at the distal end of the introducer.

9. The medical device according to claim 8, wherein the effector comprises at least one of a nozzle, a valve, an orifice, an aperture, a fissure, or a slot.

10. A medical device comprising:
    an introducer extending along a longitudinal axis and having a proximal end, a distal end, an internal lumen extending from the proximal end to the distal end and defining a first cross-sectional diameter in a plane substantially perpendicular to the longitudinal axis, and a constricted section within the internal lumen defining a second cross-sectional diameter in a plane substantially perpendicular to the longitudinal axis that is less than the first cross-sectional diameter;
    an effector located at the distal end of the introducer;
    a first section configured to connect to a canister of therapeutic fluid, the first section disposed adjacent to the proximal end of the introducer;
    a second section including an introduction port configured to connect to a supply of therapeutic elements, the second section connected to the introducer at the constricted section, the therapeutic elements comprising solid particles that are implantable within human body tissue; and an expander located between the first section and the constricted section;

wherein the expander is configured to lower a temperature of the therapeutic fluid to a cryogenic temperature lower than a temperature of the therapeutic elements;

wherein the introduction port includes a passageway that is in fluid communication with the constricted section of the introducer such that, during use, the therapeutic elements are drawn into the introducer by way of a venturi effect created by a flow of the therapeutic fluid through the introducer; and wherein the effector is configured to discharge the therapeutic elements within a body cavity.

11. The medical device according to claim 10, wherein the therapeutic fluid is nitric oxide.

12. The medical device according to claim 10, wherein the expander is operable to reduce the temperature of the therapeutic fluid to −20 degrees Celsius.

13. The medical device according to claim 10, wherein the therapeutic elements are metal balls.

14. The medical device according to claim 10, wherein the therapeutic elements are configured to release a therapeutic agent after being implanted in an anatomical feature.

15. A method comprising:

directing a flow of therapeutic fluid through an introducer lumen, into a uterine cavity, and toward an intrauterine wall, wherein the therapeutic fluid is introduced at a proximal portion of the introducer lumen and is expelled into the uterine cavity at a distal portion of the introducer lumen, the introducer lumen further including a constricted section between the proximal portion and the distal portion;

reducing a temperature of the therapeutic fluid to a first temperature by passing the flow of therapeutic fluid through an expander located between the proximal portion and the constricted section, wherein the first temperature is a cryogenic temperature;

introducing therapeutic elements having a second temperature into the flow of the therapeutic fluid having the first temperature, at the constricted section, to create a mixture including the therapeutic fluid and the therapeutic elements, wherein the second temperature is greater than the first temperature, and wherein the therapeutic elements comprise solid particles; and embedding the therapeutic elements into the intrauterine wall.

16. The method according to claim 15, wherein the method comprises reducing a temperature of the therapeutic elements before introducing the therapeutic elements into the flow of the therapeutic fluid.

17. The method according to claim 15, wherein the introducer lumen extends from a proximal end to a distal end along a longitudinal axis and defines a first cross-sectional diameter in a plane substantially perpendicular to the longitudinal axis, and wherein the constricted section defines a second cross-sectional diameter in a plane substantially perpendicular to the longitudinal axis that is less than the first cross-sectional diameter.

18. The method according to claim 15, wherein the mixture including the therapeutic fluid and the therapeutic elements is created at the constricted section of the introducer lumen by a venturi effect.

19. The medical device according to claim 1, wherein the second section is spaced distally from the first section.

* * * * *

UNITED STATES PATENT AND TRADEMARK OFFICE
CERTIFICATE OF CORRECTION

PATENT NO. : 11,717,656 B2
APPLICATION NO. : 16/358818
DATED : August 8, 2023
INVENTOR(S) : Murdeshwar et al.

It is certified that error appears in the above-identified patent and that said Letters Patent is hereby corrected as shown below:

On the Title Page

Item (73), in "Assignee", in Column 1, Line 1, delete "Gyros ACMI" and insert --Gyrus ACMI,-- therefor On page 2, in Column 2, item (56), under "Other Publications", Line 10, delete "fled" and insert --filed-- therefor In the Specification In Column 4, Line 4, delete "–20 degrees," and insert -- –20 degrees Celsius,-- therefor In Column 4, Line 5, after "–90", insert --degrees--

In Column 5, Line 20, delete "–20 degrees," and insert -- –20 degrees Celsius,-- therefor In Column 5, Line 21, after "–90", insert --degrees--

In Column 7, Line 12, after "–90", insert --degrees--

In Column 7, Line 60, delete "26" and insert --42-- therefor

In Column 7, Line 60, delete "28." and insert --44.-- therefor

In Column 7, Line 62, delete "28." and insert --44.-- therefor

Signed and Sealed this
Nineteenth Day of September, 2023

Katherine Kelly Vidal
*Director of the United States Patent and Trademark Office*